United States Patent
Koivisto et al.

(10) Patent No.: US 12,367,963 B2
(45) Date of Patent: Jul. 22, 2025

(54) SYSTEMS AND METHODS TO IDENTIFY AND UTILIZE CORRELATIONS BETWEEN CONTENT CLASSIFICATIONS AND PSYCHOLOGICAL PROFILES OF USERS TO PROVIDE AN ADAPTABLE DIGITAL ENVIRONMENT

(71) Applicant: Solsten, Inc., Edina, MN (US)

(72) Inventors: Jonna Maarit Koivisto, Berlin (DE); Joseph Jack Schaeppi, Maple Grove, MN (US)

(73) Assignee: Solsten, Inc., Edina, MN (US)

( * ) Notice: Subject to any disclaimer, the term of this patent is extended or adjusted under 35 U.S.C. 154(b) by 466 days.

(21) Appl. No.: 17/971,093

(22) Filed: Oct. 21, 2022

(65) Prior Publication Data
US 2024/0136048 A1 Apr. 25, 2024
US 2024/0233910 A9 Jul. 11, 2024

(51) Int. Cl.
*G16H 20/70* (2018.01)
(52) U.S. Cl.
CPC .................. *G16H 20/70* (2018.01)
(58) Field of Classification Search
CPC .................................................. G16H 20/70
See application file for complete search history.

(56) References Cited

U.S. PATENT DOCUMENTS

| | | | |
|---|---|---|---|
| 8,346,781 B1 | 1/2013 | Cornelius | |
| 2002/0029162 A1* | 3/2002 | Mascarenhas | G06Q 30/0203 707/E17.109 |
| 2012/0059785 A1* | 3/2012 | Pascual Leo | G06Q 30/02 706/50 |
| 2013/0290207 A1* | 10/2013 | Bonmassar | G06Q 10/1053 705/321 |
| 2014/0324749 A1* | 10/2014 | Peters | G09B 7/04 706/46 |

(Continued)

FOREIGN PATENT DOCUMENTS

WO WO-2022019558 A1 * 1/2022

OTHER PUBLICATIONS

PCT International Search Report and Written Opinion for Application No. PCT/US23/76614, mailed Jan. 22, 2024 ( 9 pages).

*Primary Examiner* — William L Bashore
*Assistant Examiner* — Gregory A Distefano
(74) *Attorney, Agent, or Firm* — Esplin & Associates, PC

(57) ABSTRACT

Systems and methods to identify and utilize correlations between content classifications and psychological profiles of users to provide an adaptable digital environment are disclosed. Exemplary implementations may: obtain interaction information; determine, based on the interaction information, content-specific correlations between psychological parameter value(s) and/or the individual psychological profiles of individual users and individual pieces of content; determine content classes and content subclasses that characterize the individual pieces of content; determine, based on the content-specific correlations, master-correlations between the content class(es) and/or the content subclass(es) and a strength of the individual one or more psychological parameter values relative to other ones of the psychological parameter values included in the psychological profiles; determine individual predicted responses to the individual pieces of content based on strengths of the master-correlations, the psychological profiles of the master-correlations, and the interaction information; identify and present prospective pieces of content for the users based on the predicted responses.

14 Claims, 3 Drawing Sheets

(56) References Cited

U.S. PATENT DOCUMENTS

| | | | |
|---|---|---|---|
| 2015/0356261 A1* | 12/2015 | Brust | G16Z 99/00 |
| | | | 705/2 |
| 2017/0017644 A1* | 1/2017 | Accardo | G06F 16/285 |
| 2020/0082928 A1* | 3/2020 | Wu | G16H 70/20 |
| 2021/0350202 A1 | 11/2021 | Zachariah | |
| 2021/0379495 A1 | 12/2021 | Schaeppi | |
| 2021/0397613 A1* | 12/2021 | Swint | G06N 3/084 |
| 2022/0238204 A1 | 7/2022 | Schaeppi | |
| 2022/0239653 A1 | 7/2022 | Schaeppi | |

* cited by examiner

SYSTEMS AND METHODS TO IDENTIFY AND UTILIZE CORRELATIONS BETWEEN CONTENT CLASSIFICATIONS AND PSYCHOLOGICAL PROFILES OF USERS TO PROVIDE AN ADAPTABLE DIGITAL ENVIRONMENT

FIELD OF THE DISCLOSURE

The present disclosure relates to systems and methods to identify and utilize correlations between content classifications and psychological profiles of users to provide an adaptable digital environment.

BACKGROUND

Existing systems may adapt digital environments for users based on how the users interact with content presented via the digital environments. These existing system may fail to consider content classes and content subclasses that individual pieces of content may be classified into.

SUMMARY

One aspect of the present disclosure relates to a system configured to identify and utilize correlations between content classifications and psychological profiles of users to provide an adaptable digital environment. Individual pieces of content may be classified into various content classes and/or subclasses that conform to a unique taxonomy. Based on how the users interact with pieces of content and the psychological parameter values or the psychological profiles of the users, content-specific correlations may be determined between individual pieces of content and one or more psychological parameter values. Based on these content-specific correlations, master-correlations may be determined between the content class/subclass classifications of the pieces of content included in the content-specific correlations and strengths of the one or more psychological parameter values. Based on the master-correlations, interaction information collected, monitored, and stored, predicted responses to the pieces of content may be determined. Subsequently, based on the predicted responses, active content in the users' digital environments, the content classes/subclasses of the pieces of content, prospective content may be determined and appropriately presented to the users. As such, a computer system may monitor multiple users' interactions with various pieces of content that are classified into content classes/subclasses and adjust the content presented to the users appropriately.

The system may include electronic storage, one or more hardware processors configured by machine-readable instructions, and/or other elements. The machine-readable instructions may include one or more instruction components. The instruction components may include computer program components. The instruction components may include one or more of information obtaining component, correlation determination component, content class determination component, master-correlation determination component, response determination component, content identifying component, presentation component, and/or other instruction components The electronic storage may store taxonomical classifications of individual pieces of content, psychological profiles for users of digital environments, and/or other information. Individual ones of the taxonomical classifications may include content classes and content subclasses to the content classes for the individual pieces of content. The taxonomical classifications may conform to a taxonomy that defines a hierarchical system of the content classes and the content subclasses. The pieces of content may be characterized by the classifications into the content classes and the content subclasses. The psychological profiles may include psychological parameter values for psychological parameters.

The information obtaining component may be configured to obtain interaction information from online platforms that provide the digital environments. Individual interaction information may specify instances of interactions between individual users and/or individual psychological profiles of the individual users, and one or more pieces of content via the digital environments and timing information for the instances, and/or other interaction information.

The correlation determination component may be configured to determine, based on the interaction information and/or other information, content-specific correlations between one or more of the psychological parameter values of the individual users and/or the individual psychological profiles of the individual users, and the individual pieces of content.

The content class determination component may be configured to determine the content classes and the content subclasses that characterize the individual pieces of content included in the content-specific correlations.

The master-correlation determination component may be configured to determine, based on the content-specific correlations and/or other information, master-correlations between one or more of the content classes and/or the content subclasses and a strength of individual ones of the one or more psychological parameter values or a combination of the psychological parameter values included in the psychological profiles relative to other ones of the psychological parameter values included in the psychological profiles.

The response determination component may be configured to determine individual predicted responses to the individual pieces of content classified in the one or more content classes and/or the content subclasses that are included in the master-correlations based on strengths of the master-correlations, the psychological profiles included in the master-correlations, the interaction information, and/or other information.

The content identifying component may be configured to identify prospective pieces of content for the users based on the predicted responses, the pieces of content that are active in the digital environments, the taxonomical classifications of the individual pieces of content, the psychological profiles of the users, and/or other information.

The presentation component may be configured to effectuate presentation of the prospective pieces of content to the users within the digital environments.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
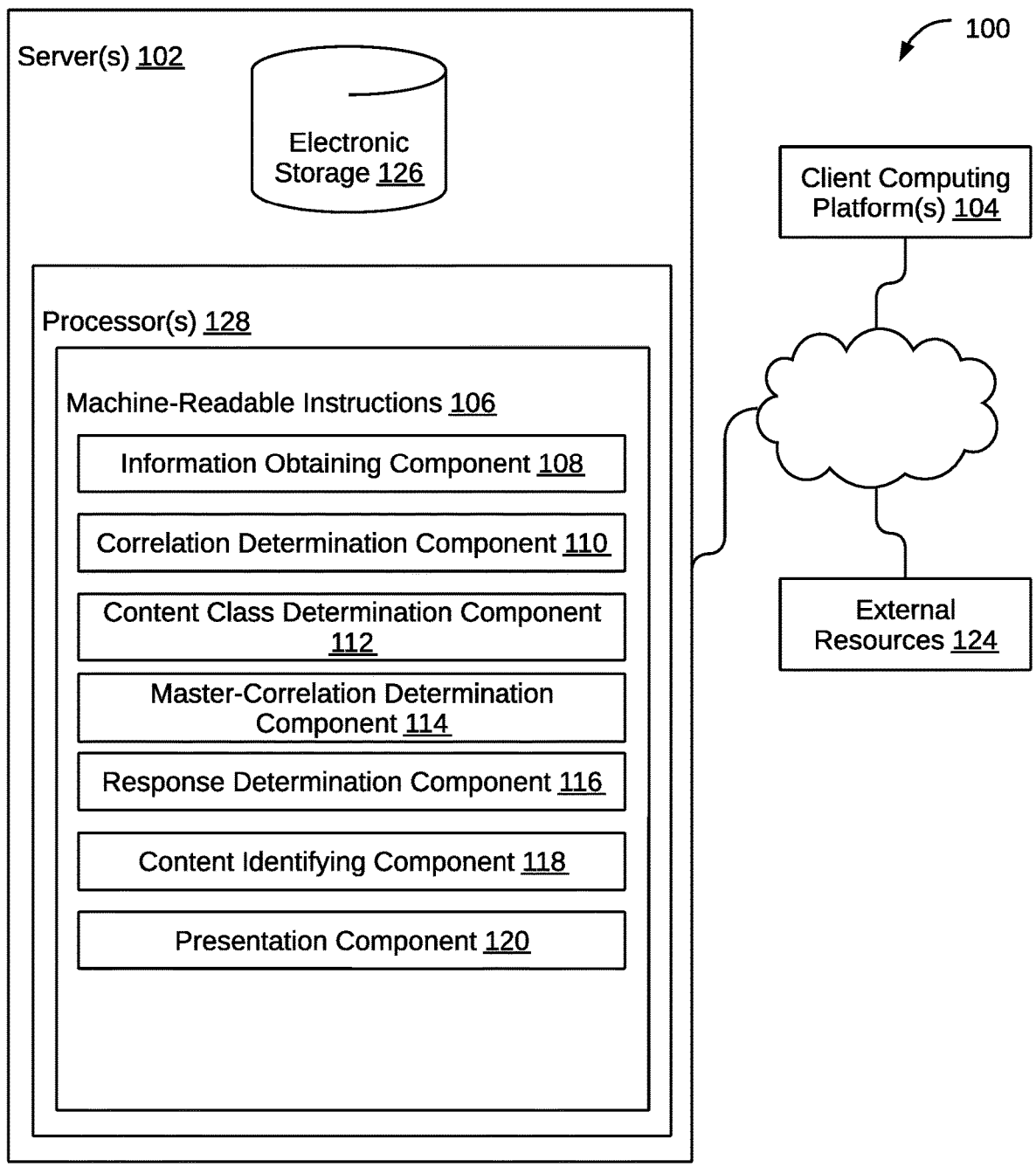
FIG. 1 illustrates a system configured to identify and utilize correlations between content classifications and psychological profiles of users to provide an adaptable digital environment, in accordance with one or more implementations.

FIG. 1 illustrates a system 100 configured to identify and utilize correlations between content classifications and psychological profiles of users to provide an adaptable digital environment, in accordance with one or more implementations. In some implementations, system 100 may include one or more servers 102, electronic storage 126, and/or other elements. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Electronic storage 126 may store taxonomical classifications of individual pieces of content, psychological profiles for users of digital environments, and/or other information. Individual taxonomical classifications may include content classes and content subclasses to the content classes for the individual pieces of content. The taxonomical classifications may conform to a taxonomy that defines a hierarchical system of the content classes and the content subclasses. The pieces of content may be characterized by the classifications into the content classes and the content subclasses.

The pieces of content may include a character, a game, a game asset, video content, image content, and/or other pieces of content. The character may refer to an object (or group of objects) present in a virtual space that corresponds to an individual user (e.g., an avatar) and/or are controlled by the user. In some implementations, the character may not correspond to an individual user but rather provide information (e.g., the recommendation, the suggestion) to the user. The game asset may include a virtual item, a virtual resource (e.g., weapon, tool), of in-game powers, in-game skills, in-game technologies, and/or other game assets.

The digital environments may be hosted by or otherwise provided by the online platforms. In some implementations, the digital environments may be accessible via applications. The applications may include mobile applications accessible via portable client computing platforms 104, desktop applications, console applications, television applications, and/or other applications. In some implementations, the online platforms may be directly accessed via web browsers and Internet, or offline. For example, the digital environments, and types thereof, may include, by way of non-limiting example, game environments, educational environments, reading environments, music interfaces, social networking environments, entertainment environments, fitness environments, business environments, shopping environments, food & drink providing environments, among others integrated or connected with system 100.

The digital environment and/or individual applications may provide simulated spaces or views of a virtual space. Individual simulated spaces may have a topography, express ongoing real-time interaction by one or more users, and/or include one or more objects positioned within the topography that are capable of locomotion within the topography. In some instances, the topography may be a 2-dimensional topography. In other instances, the topography may be a 3-dimensional topography. The topography may include dimensions of the space, and/or surface features of a surface or objects that are "native" to the space. In some instances, the topography may describe a surface (e.g., a ground surface) that runs through at least a substantial section of the space. In some instances, the topography may describe a volume with one or more bodies positioned therein (e.g., a simulation of gravity-deprived space with one or more celestial bodies positioned therein). The instance executed by the computer components may be synchronous, asynchronous, and/or semi-synchronous.

Some of the content classes may be high order classes and some of the content classes may be lower order subclasses. That is, a high order class may include more specific lower order subclasses where classification into the subclasses more specifically describe the content as further content subclasses exist for the lower order subclasses. In some implementations, a given (sub)class may be one or more hierarchical orders within the taxonomy. The content classes may include genre, platform-specific genre, mechanics, theme, art style and perspective, brand intellectual property, modes, churn, marketing assets, creative elements, and/or other content classes and subclasses. These content classes may be the highest order of classes of the content classes and subclasses. By way of non-limiting example, each of these content classes may include one or more lower order content subclasses.

A given genre may refer to a particular style, form, or set of content elements (.e.g., action, adventure, sports, casino). A given platform-specific genre may a genre specific to a platform and/or real or virtual setting (e.g., arcade, music, party, racing, slots). A given mechanic may govern rules for the users and responses to actions by the users and/or actions of other pieces of content within the digital environment (e.g., physics). A given theme may refer to a particular subject or topic that the digital environment is related and developed around (e.g., crime/mystery, horror, vehicles). A given art style and perspective may refer to visual style, render technique, perspective, and/or other art styles and/or perspectives. A given brand intellectual property may refer to tangible or intangible concepts that may be affiliated with a brand (e.g., sports, game show, kids toy). A given mode may refer to a configuration of a digital environment and a role or position of the user/player within the digital environment (e.g., player-as-manager, single player, player-as-actor). A given churn may refer to how the users and/or content within the digital environment move in and out of the digital environment (e.g., deliberate). A given marketing asset may refer to an element that may facilitate promotion or presentation of a piece of content (e.g., placements, emotional drivers). A given creative element may refer to an artistic element that facilitate promotion of a piece of content (e.g., coin, flag, light bulb). The content classes and subclasses may be associated with a binary number, a yes or no, and/or other type of value.

In some implementations, a given psychological profile may characterize and be for a single unique user. In some implementations, the given psychological profile may characterize and be for more than one user. The psychological profiles may include the psychological parameter values to the psychological parameters. The psychological profiles may include sets of psychological parameter values to the psychological parameters for the individual users. By way of non-limiting example, the psychological parameter values of the psychological parameters may be a number score on a predetermined range unique to each psychological parameter, a letter score, and/or other type of value than may characterize a particular user as whole.

Parameters, such as psychological parameters are described herein, may specify measurable, recordable, and/or determined information. The parameter values corresponding to the parameters may be a particular value, numerical or non-numerical, that characterizes the content, the users, or respective element that the parameter value is described in relation to. The psychological parameter values may characterize a given users feelings, emotions, perceptions, thoughts, and behaviors. By way of non-limiting example, the psychological parameters values may characterize competitiveness, goal orientation, and learning style, among others.

Server(s) 102 may be configured by machine-readable instructions 106. Machine-readable instructions 106 may include one or more instruction components. The instruction components may include computer program components. The instruction components may include one or more of information obtaining component 108, correlation determination component 110, content class determination component 112, master-correlation determination component 114, response determination component 116, content identifying component 118, presentation component 120, and/or other instruction components.

Information obtaining component 108 may be configured to obtain interaction information from the online platforms that provide the digital environments. The interaction information may characterize interactions between the users and the pieces of content via the digital environments and/or engagement by the users with the pieces of content. The individual interaction information may specify i) instances of interactions between individual users and/or individual psychological profiles of the individual users, and one or more pieces of content via the digital environments, ii) timing information for the instances, and/or other information. In some implementations, the interaction information may be obtained in an ongoing manner from multiple online platforms for multiple users at once. The term "ongoing manner" as used herein may refer to continuing to perform an action (e.g., obtain) periodically (e.g., every 30 seconds, every minute, every hour, etc.) until receipt of an indication to terminate. The indication to terminate may include powering off system 100, shutting down the online platforms, resetting system 100, and/or other indications of termination. Thus, the instances of interactions may be collected, obtained, received, monitored, and/or analyzed.

The instances of interactions may include the content engaged with by the users, how the individual users engaged with the content, content not engaged with or avoided by the users, and/or other interaction information. In some implementations, the interaction information may identify the users. In some implementations, the interaction information may identify the psychological profiles of the users. The content engaged with by the individual users may be related to the digital environments or the individual online platforms that provide the content. That is, for example, the content provided by the digital environment may relate to online games (e.g., virtual goods, virtual mini games, etc.) the digital environment hosts. In some implementations, the content engaged with by the individual users may not be related to the digital environments that provide the content. Meaning, the content may direct the user to a different digital environment.

How the users engage with the content, or engagement by the individual users, may define behavior patterns of the individual users with or based on the content. The behavior patterns may include consecutive actions of the users within the digital environments, with other ones of the users within the digital environments, and with content within the digital environments. The behavior patterns may indicate spending patterns of the users, completed tasks by the individual users, uncompletion tasks by the individual users, failure of tasks by the individual users, game mechanics initiated by the users, and/or other behavior patterns. The actions may include one or more of a purchase based on the content, a sale, a trade, a donation, a user selection of the content, gameplay (e.g., mini-game, battle, competition, etc.) based on the content, communication of the individual users with other particular users or users, completion of tasks by the users, frequent interaction with the content, formation of alliances by the users, and/or other actions. The spending patterns may indicate an amount of currency (e.g., real-world money, virtual money, points, etc.) spend, an amount of currency earned, an amount of currency donated, and/or other indications.

The game mechanics may include alternating turns in the one or more games, action points, playing cards, capturing, catch-up progression, dice, movements, resource management, risk and reward, role-playing, game modes (e.g., single-player, multiplayer), and/or other novel or known game mechanics. In some implementations, different ones of the games and/or the content provided by the online platforms via the digital environments may employ different game mechanics. Thus, the user may initiate and utilize different game mechanics within the digital environments. Conversely, the user may disregard some of the game mechanics by disregarding some of the games and/or the content within the digital environments.

The timing information may include time spent by the individual users engaging/interacting with the content, the other users, and/or within the digital environment, frequency of subsequent re-interaction or initiation of subsequent instances, a time of day of the instances, a time of week of the instances, a time of year of the instances, special occasions during or near the instances (e.g., user's birthday, federal holidays), and/or other timing information.

By way of non-limiting example, interaction information obtaining component 108 may be configured to obtain first interaction information that specifies at least a first instance of an interaction between a first user and a first piece of content via the digital environments, timing information for the first instance, and/or other information. The first user may be associated with a first psychological profile. The first piece of content may be classified with a first content class and a first content subclass of a second content class.

In some implementations, information obtaining component 108 may be configured to receive predicted responses via client computing platform 104 associated with an administrative user. The administrative user may be associated with a given online platform. The predicted responses received may be responses to elicit by way of particular pieces of content presented to a given user or users via the digital environments.

Correlation determination component 110 may be configured to determine content-specific correlations. The content-specific correlations may be between i) one or more of the psychological parameter values included in the psychological profiles the individual users or the individual psychological profiles of the individual users, and ii) the individual pieces of content. Determination of the content-specific correlations may be based on the interaction information and/or other information. That is, based on the pieces of content that the users engage with, how they engage, and the timing information of the instances of interactions, the content-specific correlations may be determined. The various interaction information may indicate similar timing information, similar behavior patterns, a majority similarity of the psychological profiles, identical ones of the psychological profiles for different users, pieces of content with a common content class/subclass, pieces of content with a majority similar taxonomical classifications, pieces of content with identical taxonomical classifications, and/or other similarities that provide a basis to the content-specific correlations. A majority similarity may include psychological parameter values associated with different users to the same psychological parameter that are within a particular range, a particular amount of psychological parameter values that are within the particular range or identical, a particular amount of the content class/subclasses that are the same, and/or other majority thresholds.

In some implementations, a content-specific correlation may be between a single psychological parameter value to a psychological parameter or a set of psychological parameter values to psychological parameters, and an individual piece of content. In some implementations, a content-specific correlation may be between a psychological profile and an individual piece of content. Meaning, the set of psychological parameters and their psychological parameter values that comprise the entire psychological profile may be correlated with the individual piece of content. By way of non-limiting example, correlation determination component 110 may be configured to determine, based on the first interaction information and other ones of the interaction information, a first content-specific correlation between the first psychological profile and the first piece of content.

It will be appreciated that the description herein of "correlations" between the one or more psychological parameter values or the individual psychological profiles, and a piece of content which are positively correlated is not intended to be limiting, and that negative correlations between the one or more psychological parameter values or the individual psychological profiles, and the piece of content are also contemplated, and may be included in the generic "correlations". The determination of negative correlations may be made in cases where users strongly presenting a psychological parameter avoid a specific piece of content, and/or where users that do not present the psychological parameter interact with the specific piece of content relatively more (e.g., in frequency, total performances, etc.) than other users that strongly present the psychological parameter.

Content class determination component 112 may be configured to determine the content classes and the content subclasses that characterize the individual pieces of content included in the content-specific correlations. The content classes and the content subclasses may be determined based on the stored information in electronic storage 126. By way of non-limiting example, content class determination component 112 may be configured to determine the content classes and the content subclasses that characterize the first piece of content. The first piece of content may be classified into the first content class and the first content subclass of the second class, for example.

Master-correlation determination component 114 may be configured to determine master-correlations. The master-correlations may be determined based on the content-specific correlations. The master-correlations may be between i) one or more of the content classes and/or the content subclasses (included in the content-specific correlations), and ii) a strength of individual ones of the psychological parameter values or a combination of the psychological parameter values included in the psychological profiles (included in the content-specific correlations). The strength may be relative to other ones of the psychological parameter values included in the psychological profiles. In some implementations, the strength of a given psychological parameter value to a given psychological parameter relative to the other psychological parameter values may signify a greater presence of the given psychological parameter value in comparison with the other psychological parameter values included in a given psychological profile. In some implementations, the strength of a given psychological parameter value to a given psychological parameter relative to the other psychological parameter values may signify a greater presence of the given psychological parameter value in comparison with psychological parameter values to the given psychological parameter included in the psychological profiles stored in electronic storage 126.

In some implementations, the strength of a combination of the psychological parameter values relative to other psychological parameter values may signify a greater presence of the given combination in comparison with the other psychological parameter values included in a given psychological profile. In some implementations, the strength of a given combination relative to the other psychological parameter values may signify a greater presence of the given combination in comparison with psychological parameter values to the given psychological parameter included in the psychological profiles stored in electronic storage 126.

The strength of the psychological parameter value or the combination may be determined by analyzing the psychological parameter values included in the given psychological profile or included in the all the psychological profiles stored in electronic storage 126. The analysis may include determining whether the psychological profiles or the given psychological profile include psychological parameter values to the given psychological parameter or the combination, and determining the strength amongst the existing psychological parameter values. A maximum strength may be determined, and a minimum strength may be determined.

By way of non-limiting example, master-correlation determination component 114 may be configured to determine, based on the first content-specific correlation and other ones of the content-specific correlations, a first master-correlation. The first master-correlation may be between at least the first content class and the first content subclass that characterize the first piece of content, and a strength of the individual psychological parameter values or a combination of the psychological parameter values relative to other ones of the psychological parameter values that the first psychological profile and other ones of the psychological profiles include (e.g., a first psychological parameter value to a first psychological parameter).

Response determination component 116 may be configured to determine individual predicted responses to the individual pieces of content classified in the one or more content classes and/or the content subclasses that are included in the master-correlations. The predicted responses may be response that are expected from users upon interaction with such individual pieces of content. By way of non-limiting example, the predicted responses may include purchasing a given piece of content upon discovery or presentation, collecting the given piece of content to gift, viewing a given piece of visual content, sharing the given piece of visual content, playing a game content until they beat it, and/or other responses.

The predicted responses may be determined based on strengths of the master-correlations, the interaction information, the psychological profiles included in the master-correlations, and/or other information. The strengths of the master-correlations may be determined based on a particular frequency of determination of the same master-correlation, a majority of the content classes/subclasses and/or the psychological parameter values being the same, a majority of the content classes/subclasses being the same and a majority of the psychological parameter values being with a particular range, and/or other determinations. The particular range may be predefined. The individual content class and the individual content subclasses may be associated with one or more predicted responses from the users that interact with content of those classifications.

By way of non-limiting example, response determination component 116 may be configured to determine one or more predicted responses to the first piece of content based on a strength of the first master-correlation, the first psychological profile, and the taxonomical classifications of the first piece of content. That is, the strength of the first master-correlation indicating that pieces of content classified under the first content class and the first content subclass are strongly correlated to the first psychological parameter value to the first psychological parameter, may be evident and/or determined. The interaction information may include instances of interactions between the users with the psychological profiles and different pieces of content. Thus, the interaction information that includes psychological profiles including the first psychological parameter value to the first psychological parameter may be determined. These particular interaction information may facilitate in determination of the predicted responses to the pieces of content classified under the first content class and the first content subclass by the users.

Content identifying component 118 may be configured to identify prospective pieces of content for the users based on the predicted responses, the pieces of content that are active in the digital environments, the taxonomical classifications of the individual pieces of content, the psychological profiles of the users, and/or other information. The prospective pieces of content may be one or more of the pieces of content that may be presented to the users via the digital environment because they are appropriate for the users. The pieces of content that are active may be the pieces of content that are being presented to the users or are discoverable by the users with the digital environments. In some implementations, the identification of the prospective pieces of content may be based on the predicted responses received from the administrative user. Thus, given the strengths of the psychological parameter values included in the psychological profiles of the users, the various content classes and content subclasses that each of the pieces of content are classified into, the content already available to the users within the digital environment, and the predicted response, the prospective pieces of content may be determined.

By way of non-limiting example, identifying the prospective pieces of content for the users may be based on at least the first master-correlation, the taxonomical classifications of the individual pieces of content, the psychological profiles of the users, and/or other information.

Presentation component 120 may be configured to effectuate presentation of the prospective pieces of content to the users within the digital environments. In some implementations, the presentation of the prospective pieces of content may include presenting the prospective content integrated into the digital environments. That is, for example, given that the digital environment is a simulation game, the prospective pieces of content may be presented or discoverable where appropriate within the simulation game. Appropriateness of presentation of discoverability of the prospective pieces of content may be based on the active pieces of content, progress of the user within the digital environment, a virtual location of the user or a character of the user within the digital environment, a time of day within the digital environment, and/or other information.

In some implementations, the presentation of the prospective pieces of content may include presenting a list of the prospective pieces of content within the digital environments. As such, the users may select which prospective pieces of content from the list to integrate into the digital environment, interact with at time of selection, remove from the list, and/or other actions related to presentation. The selection to integrate one or more of the prospective pieces of content from the list into the digital environment may cause such pieces to be presented or discoverable where appropriate within the digital environment.

Figure 3A:
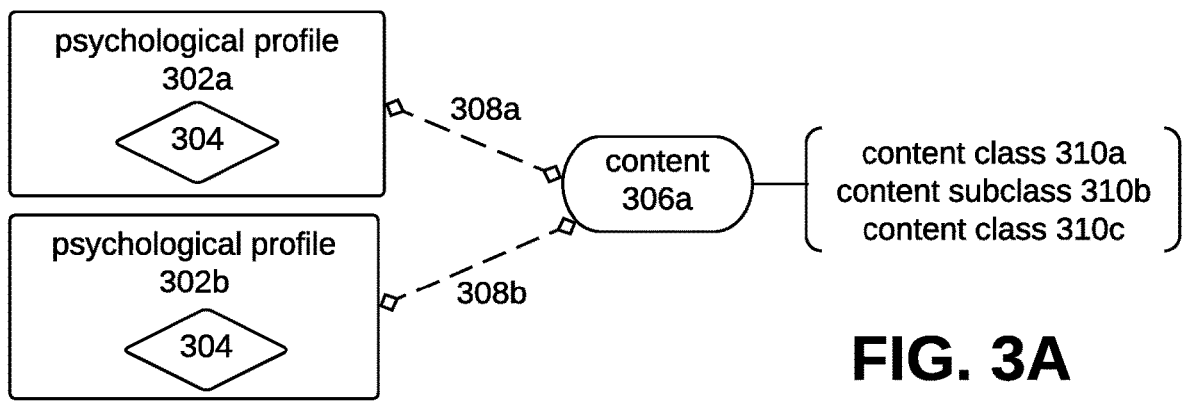
FIG. 3A-B illustrate an example implementation of the system configured to identify and utilize correlations between content classifications and psychological profiles of users to provide an adaptable digital environment, in accordance with one or more implementations.
Figure 3B:
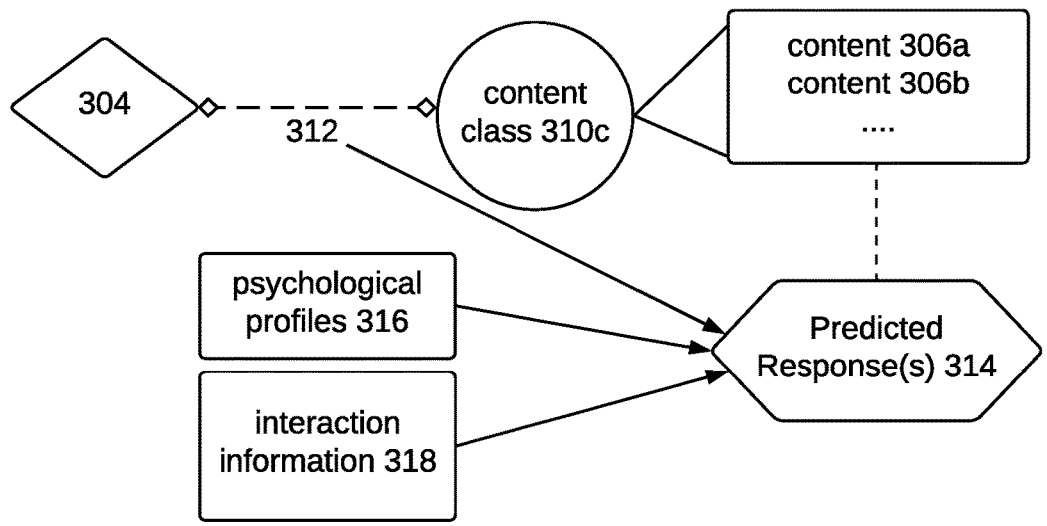
Figure 3B:
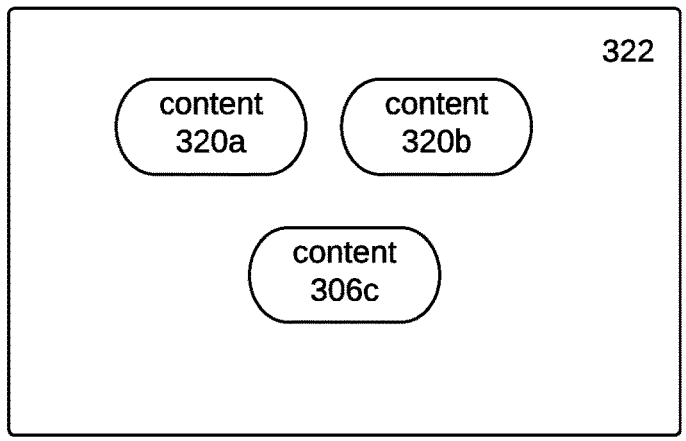

FIG. 3A-B illustrate determined content-specific correlations and master-correlations and utilization thereof. FIG. 3A illustrates a psychological profile 302a and a psychological profile 302b that both include a psychological parameter value 304 (to the same psychological parameter), e.g., high in risk-taking, among other psychological parameter values. Psychological profiles 302a and 302b may be correlated with content 306a (e.g., wearable armor) based on interaction information obtained (illustrated in FIG. 3B), e.g., users with psychological profiles 302a and 302b frequently collect, purchase, or create their own wearable armor. Thus, content-specific correlations 308a and 308b may be established. Content 306a may be classified into content class 310a (e.g., protection), content subclass 310b (e.g., wearable), and content class 310c (e.g., battles).

FIG. 3B illustrates a master-correlation 312 determined between psychological parameter value 304 from FIG. 3A and content class 310c, i.e., a taxonomical classification of content 306 in FIG. 3A. Content-specific correlations 308a and 308b in FIG. 3A may demonstrate frequency of psychological parameter value 304, and therefore strength of psychological parameter value 304. Thus, such strength of psychological parameter value 304 may be correlated with content class 310c, and establish master-correlation 312. Content 306a (same as in FIG. 3A), content 306b, and other content may be classified under content class 310c in addition to other content classes or content subclasses. Predicted response(s) 314 to content 306a and 306b may be determined based on at least a strength of master-correlation 312 (e.g., frequency of establishment of this particular correlation), psychological profiles 316, and interaction information 318 stored in accessible electronic storage (not illustrated, similar to FIG. 1 electronic storage 126). That is, particular ones of psychological profiles 316 with psychological parameter value 304 may be determined, and interaction information 318 including those particular psychological profiles 316 may be analyzed to determine predicted response(s) 314.

Prospective content 306c may be identified and presented via digital environment 322 based on content 320a and 320b actively presented in digital environment 322, predicted response(s) 314, taxonomical classification of content 320a, 320b, and 306c stored in the electronic storage, and psychological profiles 316. That is, by way of non-limiting example, based on i) predicted response(s) 314 predicting that a user may enter battles when the battles commence, ii) content 320a and 320b (e.g., a weapon and a tool) actively presented to the user via digital environment 322, and iii) content classes and/or content subclasses (i.e., the taxonomical classifications) that content 320a, 320b, 306c and other pieces of content are classified in are similar (e.g., content class 310a— battles, among others), prospective content 306c (e.g., Kevlar material) may be identified as appropriate to be presented or discoverable via digital environment 322 in addition to content 320a and 320b.

Referring back to FIG. 1, in some implementations, server(s) 102, client computing platform(s) 104, and/or external resources 124 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 124 may be operatively linked via some other communication media.

A given client computing platform 104 may include one or more processors configured to execute computer program components. The computer program components may be configured to enable an expert or user associated with the given client computing platform 104 to interface with system 100 and/or external resources 124, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a gaming console, and/or other computing platforms.

External resources 124 may include sources of information outside of system 100, external entities participating with system 100, and/or other resources. In some implementations, some or all of the functionality attributed herein to external resources 124 may be provided by resources included in system 100.

Server(s) 102 may include electronic storage 126, one or more processors 128, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 126 may comprise non-transitory storage media that electronically stores information. The electronic storage media of electronic storage 126 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 126 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 126 may include one or more virtual storage resources (e.g., cloud storage, a virtual private network, and/or other virtual storage resources). Electronic storage 126 may store software algorithms, information determined by processor(s) 128, information received from server(s) 102, information received from client computing platform(s) 104, and/or other information that enables server(s) 102 to function as described herein.

Processor(s) 128 may be configured to provide information processing capabilities in server(s) 102. As such, processor(s) 128 may include one or more of a digital processor, an analog processor, a digital circuit designed to process information, an analog circuit designed to process information, a state machine, and/or other mechanisms for electronically processing information. Although processor(s) 128 is shown in FIG. 1 as a single entity, this is for illustrative purposes only. In some implementations, processor(s) 128 may include a plurality of processing units. These processing units may be physically located within the same device, or processor(s) 128 may represent processing functionality of a plurality of devices operating in coordination. Processor(s) 128 may be configured to execute components 108, 110, 112, 114, 116, 118, and/or 120, and/or other components. Processor(s) 128 may be configured to execute components 108, 110, 112, 114, 116, 118, and/or 120, and/or other components by software; hardware; firmware; some combination of software, hardware, and/or firmware; and/or other mechanisms for configuring processing capabilities on processor(s) 128. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, 114, 116, 118, and/or 120 are illustrated in FIG. 1 as being implemented within a single processing unit, in implementations in which processor(s) 128 includes multiple processing units, one or more of components 108, 110, 112, 114, 116, 118, and/or 120 may be implemented remotely from the other components. The description of the functionality provided by the different components 108, 110, 112, 114, 116, 118, and/or 120 described below is for illustrative purposes, and is not intended to be limiting, as any of components 108, 110, 112, 114, 116, 118, and/or 120 may provide more or less functionality than is described. For example, one or more of components 108, 110, 112, 114, 116, 118, and/or 120 may be eliminated, and some or all of its functionality may be provided by other ones of components 108, 110, 112, 114, 116, 118, and/or 120. As another example, processor(s) 128 may be configured to execute one or more additional components that may perform some or all of the functionality attributed below to one of components 108, 110, 112, 114, 116, 118, and/or 120.

Figure 2:
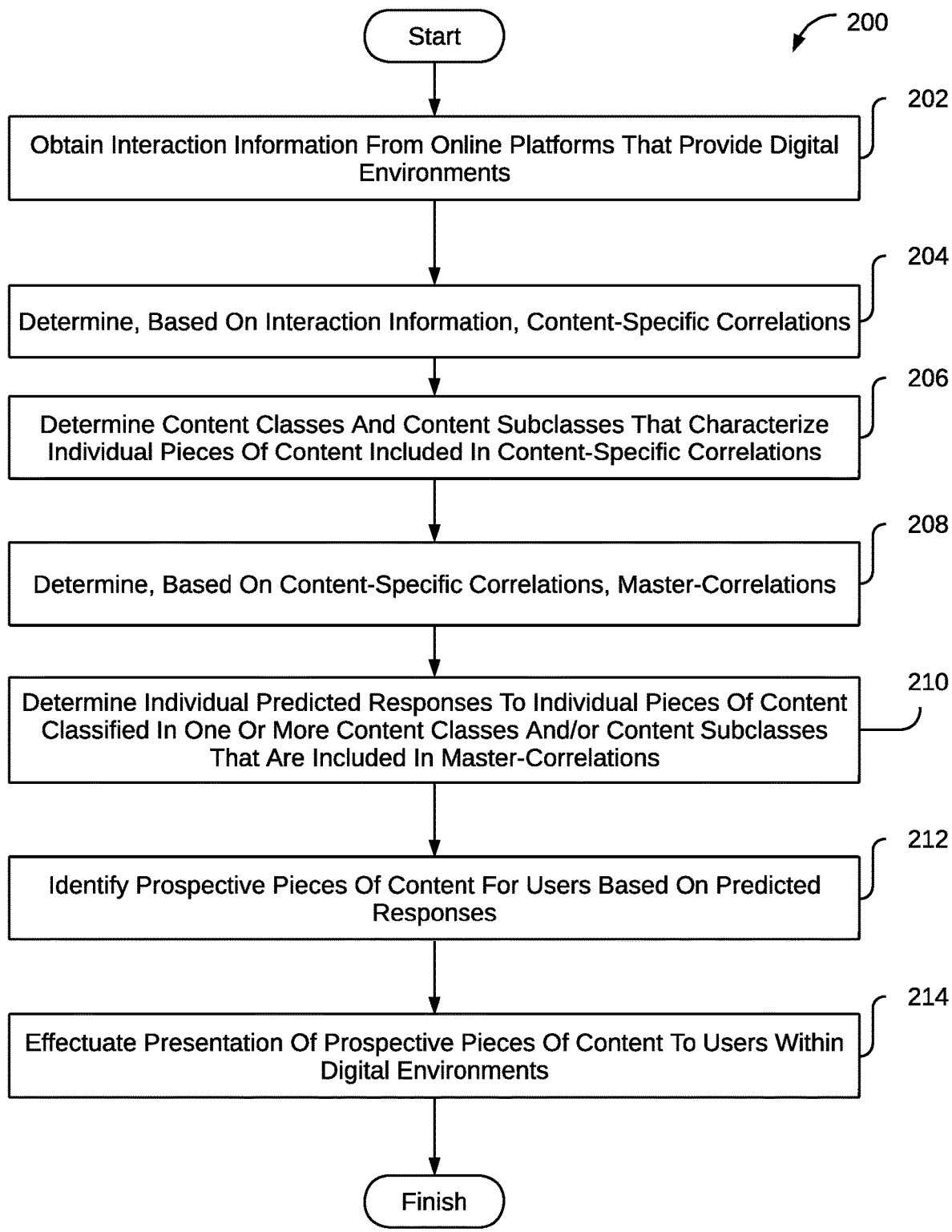
FIG. 2 illustrates a method to identify and utilize correlations between content classifications and psychological profiles of users to provide an adaptable digital environment, in accordance with one or more implementations.

FIG. 2 illustrates a method 200 to identify and utilize correlations between content classifications and psychological profiles of users to provide an adaptable digital environment, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include obtaining interaction information from online platforms that provide the digital environments. Individual interaction information specify instances of interactions between individual users and/or individual psychological profiles of the individual users, and one or more pieces of content via the digital environments and timing information for the instances. Taxonomical classifications of the individual pieces of content and the psychological profiles for users of digital environments may be stored in electronic storage. Individual taxonomical classifications may include content classes and content subclasses to the content classes for the individual pieces of content. The taxonomical classifications may conform to a taxonomy that defines a hierarchical system of the content classes and the content subclasses. The pieces of content may be characterized by the classifications into the content classes and the content subclasses. The psychological profiles may include psychological parameter values for psychological parameters. Operation 202 may be performed by one or more hardware processors configured by machine-readable instructions including a component that is the same as or similar to information obtaining component 108, in accordance with one or more implementations.

An operation 204 may include determining, based on the interaction information, content-specific correlations between one or more of the psychological parameter values of the individual users and/or the individual psychological profiles of the individual users and the individual pieces of content. Operation 204 may be performed by one or more hardware processors configured by machine-readable instructions including a component that is the same as or similar to correlation determination component 110, in accordance with one or more implementations.

An operation 206 may include determining the content classes and the content subclasses that characterize the individual pieces of content included in the content-specific correlations. Operation 206 may be performed by one or more hardware processors configured by machine-readable instructions including a component that is the same as or similar to content class determination component 112, in accordance with one or more implementations.

An operation 208 may include determining, based on the content-specific correlations, master-correlations between one or more of the content classes and/or the content subclasses and a strength of individual ones of the one or more psychological parameter values or a combination of the psychological parameter values included in the psychological profiles relative to other ones of the psychological parameter values included in the psychological profiles. Operation 208 may be performed by one or more hardware processors configured by machine-readable instructions including a component that is the same as or similar to master-correlation determination component 114, in accordance with one or more implementations.

An operation 210 may include determining individual predicted responses to the individual pieces of content classified in the one or more content classes and/or the content subclasses that are included in the master-correlations based on strengths of the master-correlations, the psychological profiles included in the master-correlations, the interaction information, and/or other information. Operation 210 may be performed by one or more hardware processors configured by machine-readable instructions including a component that is the same as or similar to response determination component 116, in accordance with one or more implementations.

An operation 212 may include identifying prospective pieces of content for the users based on the predicted responses. The pieces of content that are active in the digital environments, the taxonomical classifications of the individual pieces of content, the psychological profiles of the users, and/or other information. Operation 212 may be performed by one or more hardware processors configured by machine-readable instructions including a component that is the same as or similar to content identifying component 118, in accordance with one or more implementations.

An operation 214 may include effectuating presentation of the prospective pieces of content to the users within the digital environments. Operation 214 may be performed by one or more hardware processors configured by machine-readable instructions including a component that is the same as or similar to presentation component 120, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to identify and utilize correlations between content classifications and psychological profiles of users to provide an adaptable digital environment, the system comprising:
   electronic storage that stores i) taxonomical classifications of individual pieces of content, wherein individual taxonomical classifications include content classes and content subclasses to the content classes for the individual pieces of content, and ii) psychological profiles for users of digital environments, and wherein the taxonomical classifications conform to a taxonomy that defines a hierarchical system of the content classes and the content subclasses, wherein the individual pieces of content are characterized by the classifications into the content classes and the content subclasses, wherein the psychological profiles include psychological parameter values for psychological parameters;

one or more processors configured by machine-readable instructions to:
  obtain interaction information from online platforms that provide the digital environments, wherein the interaction information specifies i) instances of interactions via the digital environments between individual ones of the users and/or individual ones of the psychological profiles of the individual users, and one or more of the individual pieces of content, ii) timing information for the instances;
  determine, based on the interaction information, content-specific correlations between i) one or more of the psychological parameter values included in the psychological profiles of the individual ones of the users or the individual ones of the psychological profiles of the individual ones of the users, and ii) the individual pieces of content;
  determine the content classes and the content subclasses that characterize the individual pieces of content included in the content-specific correlations;
  determine, based on the content-specific correlations, master-correlations between i) one or more of the content classes and/or the content subclasses and ii) a strength of individual ones of the psychological parameter values or a combination of the psychological parameter values included in the psychological profiles relative to other ones of the psychological parameter values included in the psychological profiles;
  determine individual predicted responses to the individual pieces of content classified in the one or more of the content classes and/or the content subclasses that are included in the master-correlations based on strengths of the master-correlations, the psychological profiles included in the master-correlations, and the interaction information;
  identify prospective pieces of content for the users based on the individual predicted responses, the individual pieces of content that are active in the digital environments, the taxonomical classifications of the individual pieces of content, and the psychological profiles of the users; and
  effectuate presentation of the prospective pieces of content to the users within the digital environments, wherein the digital environments provide simulated spaces or views of a virtual space.

2. The system of claim 1, wherein the presentation of the prospective pieces of content includes integrating the prospective pieces of content into the digital environments.

3. The system of claim 1, wherein the presentation of the prospective pieces of content includes presenting a list of the prospective pieces of content within the digital environments.

4. The system of claim 1, wherein the individual pieces of content are characterized by at least a mode of user interaction, an interactivity type, a theme, and one or more subjects.

5. The system of claim 1, wherein the one or more processors are further configured by the machine-readable instructions to:
  receive the individual predicted responses via a client computing platform of an administrative user, wherein the identification of the prospective pieces of content are based on the individual predicted responses received.

6. The system of claim 1, wherein the individual pieces of content that are active are the individual pieces of content that are being presented to the users or are discoverable by the users within the digital environments.

7. The system of claim 1, wherein the one or more processors are further configured by the machine-readable instructions to:
  obtain first interaction information specifies i) a first instance of an interaction between a first user with a first psychological profile and a first piece of content via the digital environments and ii) timing information for the first instance, wherein the first piece of content is classified with a first content class and a first content subclass;
  determine, based on the first interaction information and other ones of the interaction information, a first content-specific correlation between the first psychological profile and the first piece of content;
  determine the content classes and the content subclasses that characterize the first piece of content;
  determine, based on the first content-specific correlation and other ones of the content-specific correlations, a first master-correlation between at least i) the first content class and the first content subclass that characterize the first piece of content and ii) a strength of individual ones of the psychological parameter values or a combination of the psychological parameter values relative to other ones of the psychological parameter values that the first psychological profile and other ones of the psychological profiles include; and
  determine one or more predicted responses to the first piece of content based on the first master-correlation, the first psychological profile, and the taxonomical classifications of the first piece of content, wherein identifying the prospective pieces of content for the users is based on at least a strength of the first master-correlation, the taxonomical classifications of the individual pieces of content, and the psychological profiles of the users.

8. A method to identify and utilize correlations between content classifications and psychological profiles of users to provide an adaptable digital environment, the method comprising:
  obtaining interaction information from online platforms that provide the digital environments, wherein the interaction information specifies i) instances of interactions between individual users and/or individual psychological profiles of the individual users, and individual pieces of content via the digital environments, and ii) timing information for the instances, wherein taxonomical classifications of the individual pieces of content and the psychological profiles for users of the digital environments are stored in electronic storage, wherein individual taxonomical classifications include content classes and content subclasses to the content classes for the individual pieces of content, wherein the taxonomical classifications conform to a taxonomy that defines a hierarchical system of the content classes and the content subclasses, wherein the individual pieces of content are characterized by the classifications into the content classes and the content subclasses, wherein the psychological profiles include psychological parameter values for psychological parameters;

determining, based on the interaction information, content-specific correlations between i) one or more of the psychological parameter values included in the psychological profiles of the individual users or the individual psychological profiles of the individual users, and ii) the individual pieces of content;

determining the content classes and the content subclasses that characterize the individual pieces of content included in the content-specific correlations;

determining, based on the content-specific correlations, master-correlations between i) one or more of the content classes and/or the content subclasses and ii) a strength of individual ones of the psychological parameter values or a combination of the psychological parameter values included in the psychological profiles relative to other ones of the psychological parameter values included in the psychological profiles;

determining individual predicted responses to the individual pieces of content classified in the one or more of the content classes and/or the content subclasses that are included in the master-correlations based on strengths of the master-correlations, the psychological profiles included in the master-correlations, and the interaction information;

identifying prospective pieces of content for the individual users based on the individual predicted responses, the individual pieces of content that are active in the digital environments, the taxonomical classifications of the individual pieces of content, and the psychological profiles of the users; and effectuating presentation of the prospective pieces of content to the individual users within the digital environments, wherein the digital environments provide simulated spaces or views of a virtual space.

9. The method of claim 8, wherein the presentation of the prospective pieces of content includes integrating the prospective content into the digital environments.

10. The method of claim 8, wherein the presentation of the prospective pieces of content includes presenting a list of the prospective pieces of content within the digital environments.

11. The method of claim 8, wherein the individual pieces of content are characterized by at least a mode of user interaction, an interactivity type, a theme, and one or more subjects.

12. The method of claim 8, further comprising:
receiving the individual predicted responses via a client computing platform of an administrative user, wherein the identification of the prospective pieces of content are based on the individual predicted responses received.

13. The method of claim 8, wherein the individual pieces of content that are active are the individual pieces of content that are being presented to the users or are discoverable by the users within the digital environments.

14. The method of claim 8, further comprising:
obtaining first interaction information specifies i) a first instance of an interaction between a first user with a first psychological profile and a first piece of content via the digital environments and ii) timing information for the first instance, wherein the first piece of content is classified with a first content class and a first content subclass;

determining, based on the first interaction information and other ones of the interaction information, a first content-specific correlation between the first psychological profile and the first piece of content;

determining the content classes and the content subclasses that characterize the first piece of content;

determining, based on the first content-specific correlation and other ones of the content-specific correlations, a first master-correlation between at least i) the first content class and the first content subclass that characterize the first piece of content and ii) a strength of individual ones of the psychological parameter values or a combination of the psychological parameter values relative to other ones of the psychological parameter values that the first psychological profile and other ones of the psychological profiles include; and determining one or more predicted responses to the first piece of content based on the first master-correlation, the first psychological profile, and the taxonomical classifications of the first piece of content, wherein identifying the prospective pieces of content for the users is based on at least a strength the first master-correlation, the taxonomical classifications of the individual pieces of content, and the psychological profiles of the users.

* * * * *